(12) United States Patent
Vilenskii

(10) Patent No.: US 11,813,072 B2
(45) Date of Patent: Nov. 14, 2023

(54) PORTABLE ELECTRONIC DEVICE, ACCESSORY, AND OPERATING METHOD THEREFOR

(71) Applicant: SAMSUNG ELECTRONICS CO., LTD., Suwon-si (KR)

(72) Inventor: Maxim Alexeevich Vilenskii, Moscow (RU)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 1172 days.

(21) Appl. No.: 16/348,967

(22) PCT Filed: Nov. 13, 2017

(86) PCT No.: PCT/KR2017/012777
§ 371 (c)(1),
(2) Date: May 10, 2019

(87) PCT Pub. No.: WO2018/088858
PCT Pub. Date: May 17, 2018

(65) Prior Publication Data
US 2019/0269363 A1 Sep. 5, 2019

(30) Foreign Application Priority Data

Nov. 11, 2016 (RU) .......................... RU2016144349
Nov. 7, 2017 (KR) ........................ 10-2017-0147604

(51) Int. Cl.
*A61B 5/00* (2006.01)
*G01N 21/64* (2006.01)
(Continued)

(52) U.S. Cl.
CPC ............ *A61B 5/442* (2013.01); *A61B 5/0071* (2013.01); *A61B 5/0075* (2013.01); *A61B 5/441* (2013.01);
(Continued)

(58) Field of Classification Search
None
See application file for complete search history.

(56) References Cited

U.S. PATENT DOCUMENTS 8,175,687 B2 5/2012 Kang et al.
8,496,695 B2 7/2013 Kang et al.
(Continued)

FOREIGN PATENT DOCUMENTS

JP 2006-98098 A 4/2006
JP 2008-149107 A 7/2008
(Continued)

OTHER PUBLICATIONS

Bae et al., "Multimodal facial color imaging modality for objective analysis of skin lesions". J. Biomed. Opt. 2008; 13(6): 06-4007. (Year: 2008).*
(Continued)

*Primary Examiner* — Yi-Shan Yang
(74) *Attorney, Agent, or Firm* — Sughrue Mion, PLLC

(57) ABSTRACT

Provided are a portable electronic device, an accessory, and an operation method thereof. The portable electronic device includes a light source irradiating light to skin, at least one light detector detecting light received from the skin, at least one memory storing an instruction, and a processor, by executing the instruction, controlling the light source to irradiate the light and analyzing a skin state based on light detected by the light detector.

5 Claims, 12 Drawing Sheets

(51) Int. Cl.

| | |
|---|---|
| *G01N 21/47* | (2006.01) |
| *G01N 21/25* | (2006.01) |
| *G01N 21/21* | (2006.01) |
| *G01N 21/17* | (2006.01) |

(52) U.S. Cl.
 CPC ............ *A61B 5/443* (2013.01); *A61B 5/444* (2013.01); *A61B 5/6898* (2013.01); *G01N 21/21* (2013.01); *G01N 21/255* (2013.01); *G01N 21/474* (2013.01); *G01N 21/6486* (2013.01); *G01N 2021/177* (2013.01); *G01N 2201/0221* (2013.01); *G01N 2201/0634* (2013.01); *G01N 2201/0638* (2013.01); *G01N 2201/129* (2013.01)

(56) References Cited

U.S. PATENT DOCUMENTS

| | | | |
|---|---|---|---|
| 8,705,815 B2 | 4/2014 | Chhibber et al. | |
| 9,961,247 B2 | 5/2018 | Park et al. | |
| 10,085,643 B2 | 10/2018 | Bandic et al. | |
| 2006/0183516 A1 | 8/2006 | Ham | |
| 2011/0211047 A1 | 9/2011 | Chhibber et al. | |
| 2012/0281079 A1 | 11/2012 | Chhibber et al. | |
| 2014/0304629 A1 | 10/2014 | Cummins et al. | |
| 2014/0313303 A1 | 10/2014 | Davis et al. | |
| 2014/0323873 A1 | 10/2014 | Cummins et al. | |
| 2015/0003699 A1 | 1/2015 | Davis et al. | |
| 2015/0038953 A1* | 2/2015 | Varghese | A61B 5/0077 606/9 |
| 2015/0094914 A1 | 4/2015 | Abreu | |
| 2015/0223749 A1 | 8/2015 | Park et al. | |
| 2016/0057325 A1* | 2/2016 | Park | H04N 5/2256 348/77 |
| 2016/0098614 A1 | 4/2016 | Yamanashi | |
| 2016/0357578 A1* | 12/2016 | Kim | A45D 44/005 |
| 2017/0091568 A1* | 3/2017 | Hama | G06V 10/42 |

FOREIGN PATENT DOCUMENTS

| | | |
|---|---|---|
| JP | 2008-212189 A | 9/2008 |
| JP | 2009-513230 A | 4/2009 |
| KR | 10-0481317 B1 | 4/2005 |
| KR | 10-0513156 B1 | 9/2005 |
| KR | 10-2009-0097904 A | 9/2009 |
| KR | 10-2010-0091038 A | 8/2010 |
| KR | 10-2015-0094196 A | 8/2015 |
| KR | 10-2016-0023441 A | 3/2016 |
| RU | 2 422 081 C2 | 6/2011 |
| RU | 2014 150 762 A | 7/2016 |
| WO | 2014/208185 A1 | 12/2014 |

OTHER PUBLICATIONS

Kollias et al., "Optical Non-invasive approaches to diagnosis of skin diseases". Optical Diagnosis in Dermatology, 2002, vol. 7, No. 1. pp. 64-75. (Year: 2002).*

Communication dated Dec. 20, 2021 issued by the Korean Intellectual Property Office in Korean Application No. 10-2017-0147604.

Communication dated Sep. 2, 2019 issued by the European Intellectual Property Office in counterpart European Application No. 17868710.9.

Search Report dated Jun. 26, 2017 by the Federal Service for Intellectual Property in counterpart Russian Application No. 2016144349.

Communication dated Jun. 30, 2021 issued by the Intellectual Property India in Indian Application No. 201917021779.

International Search Report dated Feb. 7, 2018 by the International Searching Authority in counterpart International Patent Application No. PCT/KR2017/012777. (PCT/ISA/210).

Written Opinion dated Feb. 7, 2018 by the International Searching Authority in counterpart International Patent Application No. PCT/KR2017/012777. (PCT/ISA/237).

Communication dated Dec. 19, 2022, issued by the Korean Intellectual Property Office in Korean Patent Application No. 10-2017-0147604.

Communication dated Jan. 27, 2023, issued by the European Patent Office in European Patent Application No. 17868710.9.

* cited by examiner

PORTABLE ELECTRONIC DEVICE, ACCESSORY, AND OPERATING METHOD THEREFOR

TECHNICAL FIELD

The present disclosure relates to a portable electronic device, an accessory, and an operation method thereof.

BACKGROUND ART

Portable electronic devices have limitations in performance due to their portability. However, with the development of technology, portable electronic devices have improved in performance to be capable of performing more complex and diverse functions. Particularly, as the performance of each device mounted in portable electronic devices improves, the number of functions capable of being performed by portable electronic devices has increased. For example, with the development of camera modules, a more accurate image may be obtained, and a processing apparatus with improved performance may analyze the accurate image at a fast speed and obtain a necessary result.

Recently, attempts have been made to analyze a skin state by using a portable electronic device with improved performance. Specifically, a variety of methods have been suggested which enables a user to conveniently analyze a skin state by using a portable electronic device, without complex and expensive measurement apparatuses or equipment.

DESCRIPTION OF EMBODIMENTS

Technical Problem

Provided are a portable electronic device which may emit light to skin and analyze a skin state by using the light reflected and/or scattered by the skin, an accessory, and an operation method thereof.

Solution to Problem

According to an aspect of the present disclosure, a portable electronic device includes a light source irradiating light to skin; at least one light detector detecting light received from the skin; at least one memory storing an instruction; and a processor, by executing the instruction, controlling the light source to irradiate the light and analyzing a skin state based on light detected by the at least one light detector.

Advantageous Effects of Disclosure

According to an embodiment, light is irradiated to skin, and a skin state may be analyzed using light reflected and/or scattered by the skin.

BRIEF DESCRIPTION OF DRAWINGS

FIG. 9 illustrates mounting of a detection shield portion (phone case).

BEST MODE

Figure 1:
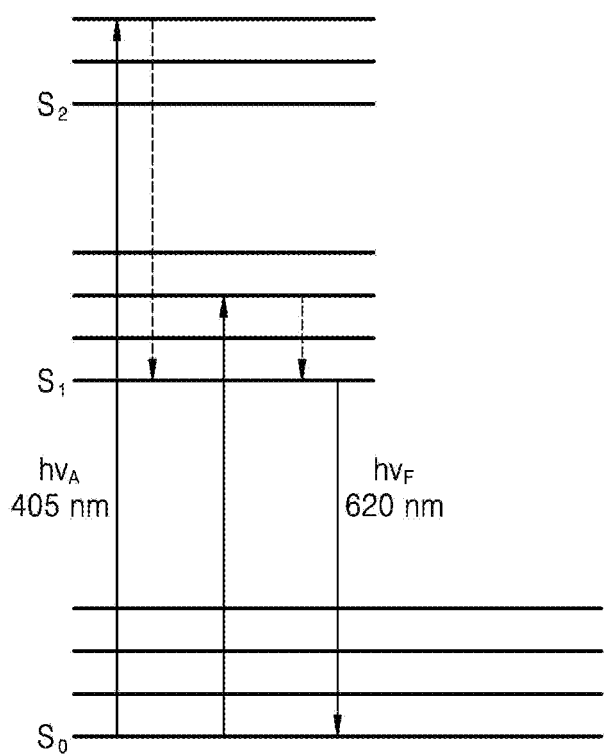
FIG. 1 illustrates energy transfer of coproporphyrin.

According to an aspect of the present disclosure, a portable electronic device includes a light source irradiating light to skin, at least one light detector detecting light received from the skin, at least one memory storing an instruction, and a processor, by executing the instruction, controlling the light source to irradiate the light and analyzing a skin state based on light detected by the at least one light detector, wherein the light received from the skin comprises at least one of light scattered, light reflected, and light emitted by the skin.

According to another aspect of the present disclosure, a method of operating a portable electronic device includes irradiating light to skin, detecting light received from the skin, and analyzing a state of the skin based on the detected light.

According to another aspect of the present disclosure, a computer program product including a recording medium having a program stored therein for performing an operation of the portable electronic device.

MODE OF DISCLOSURE

Hereinafter, embodiments of the present disclosure will be described in detail with reference to the accompanying drawings so that those skilled in the art can easily carry out the present disclosure. The present disclosure, however, may be embodied in many different forms and is not limited to the embodiments described herein. Further, in order to clearly illustrate the disclosure in the drawings, portions which are not related to the description are omitted, and like reference numerals are given to like elements throughout the specification.

Some embodiments of the present disclosure may be represented by functional block configurations and various processing steps. Some or all of these functional blocks may be implemented with various numbers of hardware and/or software configurations that perform specific functions. For example, functional blocks of the present disclosure may be implemented by one or more microprocessors, or by circuit configurations for a given function. Further, for example, the functional blocks of the present disclosure may be implemented in various programming or scripting languages. The functional blocks may be implemented with algorithms running on one or more processors. Furthermore, the present disclosure may employ conventional techniques for electronic configuration settings, signal processing, and/or data processing, and the like.

Also, connection lines or connection members between the constituent elements shown in the figures are merely illustrative of functional connections and/or physical or circuit connections. In actual devices, connections between constituent elements can be represented by various functional connections, physical connections, or circuit connections that can be replaced or added.

Also, terms such as "unit", "module", etc. stated in the specification may signify a unit to process at least one function or operation and the unit may be embodied by hardware, software, or a combination of hardware and software. However, the unit may be configured to be located in a storage medium to be addressed or configured to be able to operate one or more processors.

For example, the "unit", "module" as an example includes constituent elements such as software constituent elements, object-oriented software constituent elements, class constituent elements, and task constituent elements, processes, functions, attributes, procedures, sub-routines, segments of program codes, drivers, firmware, microcodes, circuits, data, databases, data structures, tables, arrays, and variables.

FIG. 1 illustrates energy transfer of coproporphyrin.

Porphyrins are porphine derivatives present in animals and plants and constitute hemoglobin, cytochrome, or chlorophyll. Human skin tissue contains porphyrin that is phosphor that absorbs energy of a specific wavelength and emits energy having a wavelength different from the specific wavelength. The porphyrin is also related to activities of certain bacteria in the skin. In an embodiment, to monitor a skin state, concentrations of water and porphyrin in the human skin can be monitored.

In an embodiment, in a method of analyzing a skin state, light is emitted to a target skin area, and light reflected and/or scattered by the target skin area is analyzed, thereby monitoring a distribution of water and/or porphyrin in the skin. In detail, the skin state analysis may be performed through measurement of reflectivity and color spectra of the human skin and the experimental determination of intrinsic optical parameters ($\mu_a$, $\mu_s$, g, and n) of skin and the mathematical modeling of a light propagation process in the tissue. Information about various skin components such as melanin, hemoglobin, water, carotene, and bilirubin and the existence and concentration of porphyrin in the skin may be obtained by analyzing the light reflected from the skin.

Coproporphyrin is one type of porphyrin, which contains four methyl groups and propionic acid groups in a side chain.

Referring to FIG. 1, coproporphyrin may be excited to provide fluorescence in a red area of an optical spectrum having a wavelength of about 620 nm (S0→S2). In detail, coproporphyrin may be excited by using blue light having a wavelength of about 405 nm. In this regard, the blue light having a wavelength of about 405 nm, that is, a visible spectrum range, is not dangerous to a human. The excited coproporphyrin returns to a ground state (S1→S0) and emits light having a wavelength of about 620 nm.

Figure 2:
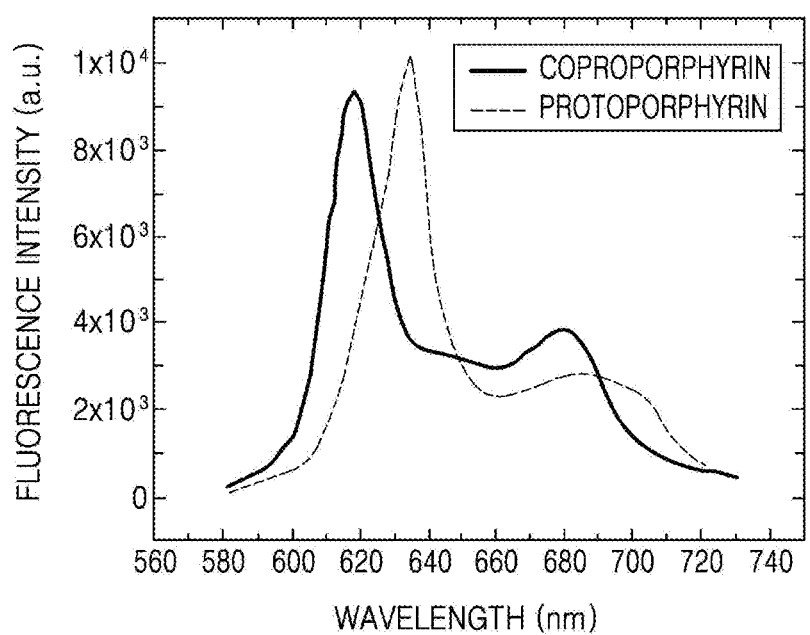
FIG. 2 illustrates fluorescence spectra of porphyrins.

FIG. 2 illustrates fluorescence spectra of porphyrins.

Protoporphyrin IX (PPIX) is another type of porphyrin that can be found in the skin, and may be generated by the body through biosynthesis of heme.

Referring to FIG. 2, fluorescence spectra obtained from two types of porphyrins, that is, coproporphyrin and protoporphyrin IX (PPIX), are illustrated.

Referring to FIG. 2, fluorescence spectra obtained from two types of porphyrins, that is, coproporphyrin and protoporphyrin IX (PPIX), are illustrated. When protoporphyrin IX, like coproporphyrin, is excited using blue light having a wavelength of about 405 nm, the protoporphyrin IX returns to the ground state and generates fluorescence in a red region of a spectrum, that is, a wavelength of about 635 nm.

In an embodiment, the excitation and emission using blue light may be used to detect existence of coproporphyrin and/or protoporphyrin IX (PPIX). Furthermore, the detection of coproporphyrin and/or protoporphyrin IX (PPIX) may be used to analyze purity of skin, activity of acne, or a potential acne appearance area.

In an embodiment, light emitted from a light source, for example, a light-emitting diode (LED), may be irradiated to the skin by passing through a first filter for transmitting light of a wavelength range that excites porphyrin. The light irradiated to the skin may interact with the skin through absorption, reflection, and scattering and then may pass through a second filter for transmitting light of a wavelength range that the excited porphyrin emits and may be received by a light detector. In this regard, the light detector may include a CMOS module or an objective lens. Then, a processor may analyze a skin state based on the detected light. The processor may perform an image intensity analysis to obtain visualized quantitative and qualitative characteristics of skin. In this regard, the processor may perform analysis by using image intensity matrix. A pixel or a pixel group having the highest intensity may characterize the concentration of protoporphyrin IX (PPIX) generated by the body through biosynthesis of heme, and the average intensity may characterizes the amount of sebum.

In detail, the processor may analyze the intensity of a pixel or a pixel group and a spatial distribution of the values thereof from images. Then, the processor may determine characteristic coefficients of dynamics related to the development of acne in the skin. Next, the processor may mark on the images the intensity of a pixel or pixel group and the spatial distribution of the values thereof, and may analyze the image to provide a visualized and biological feedback. The biological feedback denotes dependency according to the brightness of a pixel or a pixel group with respect to visualization parameters of porphyrin. The brightness of a pixel or a pixel group is proportional to the concentration of porphyrin. Accordingly, monitoring efficiency of cleaning a face may be an effective biological feedback because the monitoring may display in real time reaction of the body to external effects.

In an embodiment, the processor may display an image or coefficients of the changed skin on a screen.

According to an embodiment, the purity of skin, the activity of acne, or the potential acne appearance area may be analyzed based on the fluorescence characteristics of porphyrin. As described above, when light having a wavelength of about 405 nm is irradiated to the human skin containing porphyrin, the porphyrin may be excited to emit fluorescence by reemitting energy at a different wavelength, specifically, a wavelength of about 650 nm, thereby working as a secondary light source. Accordingly, while physically preventing detection radiation by using a narrowband filter having a center bandwidth of about 650 nm, it is necessary to record an image (a hole having fluorescent porphyrin) of an object by using a secondary light source.

Consequently, an image of a system at a bright fluorescence position corresponding to a clogged hole is generated by the fluorescence effect of porphyrin. Then, the image may be binarized, and a result image may be analyzed. The purity of skin, the activity of acne, or the potential acne appearance area may be determined based on a concentration per unit area of the intensity and/or brightness of skin at the fluorescence position.

Figure 3:
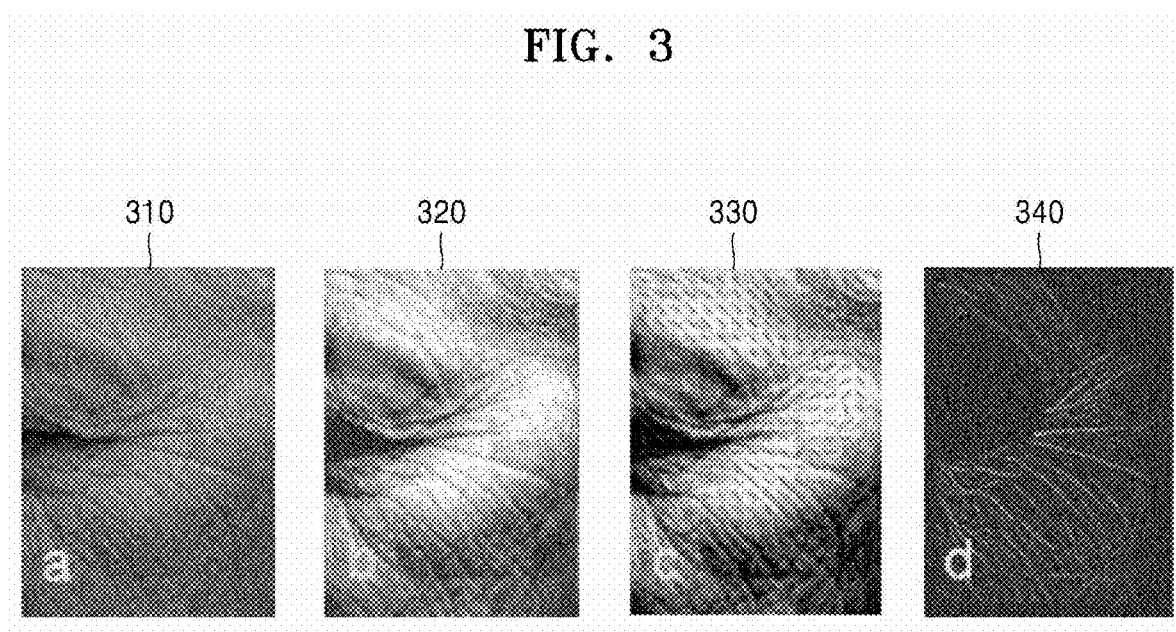
FIG. 3 illustrates a process of visualizing wrinkles, according to an embodiment.

FIG. 3 illustrates a process of visualizing wrinkles according to an embodiment.

The reflection characteristics of a human skin surface and a subsurface have dependency on the change relative to age. In other words, the surface of human skin is smoother as age decreases. Furthermore, due to the above characteristics, surface reflectivity and subsurface reflectivity of skin are higher as age decreases. According to an embodiment, by using the characteristics of polarization, a surface reflection component is removed from the skin that is known as mirror reflection from a smooth surface, and only a reflection component of a subsurface of a human may be captured and displayed as an image.

As age increases, the sebaceous gland of the human skin generates sebum less, and the skin becomes dry and dehydrates. As aged skin cells are not able to restore protection barriers, loss of water of skin increases as age increases. Human skin cells, or derma, or fibroblasts gradually lost ability of not only preserving and maintaining water and but also generating high quality collagen and resilient fiber, which leads to formation of visible wrinkles.

Wrinkle denotes a sudden depth change in a local skin surface at a specific position. In an embodiment, skin wrinkle may be measured to analyze a skin state. In this regard, a skin wrinkle measurement process may include a process of visualizing wrinkles. In the process of visualizing wrinkles, a skin surface forming component may be visualized using polarization. In detail, when linear polarization is irradiated to the skin, a transition boundary between skin and air, that is, stratum corneum, generates mirror-reflected light that preserves polarization of incident light. However some photons in a random polarization state incident on the skin intrude deep into the skin tissue before avoiding diffuse reflection and then experience subsequent scattering in the skin collagen fiber and ligament.

In polarization of a constituent element reflected by linear polarization, light division into two unrelated portions may well distinguish the visual characteristics of skin surface such as small geometrical features of skin, that is, wrinkle, a boundary higher than the periphery of a lesion, or a pore structure, from the characteristics of a subsurface of skin such as a pigment change due to melanin or flushing (erythema) of skin, thereby further facilitating skin visualization.

In a process of visualizing wrinkles according to an embodiment, parallel-polarized light is irradiated on the skin to obtain a skin image, and the obtained image is displayed on a red channel. Then, the direction of wrinkles is calculated and displayed on the obtained skin image, and finally the wrinkle may be identified so that only the wrinkle may be displayed on the skin image.

Referring to FIG. 3, an image 310 is an image obtained by irradiating parallel-polarized light on the skin, and an image 320 is an image obtained by displaying the obtained image in a red-channel. Furthermore, an image 330 is an image obtained by calculating the direction of wrinkles and displaying the calculated direction on the image 320. An image 340 is an image obtained by performing final filtering on the original copy of a normalized skin image and displaying identified wrinkles.

Figure 4:
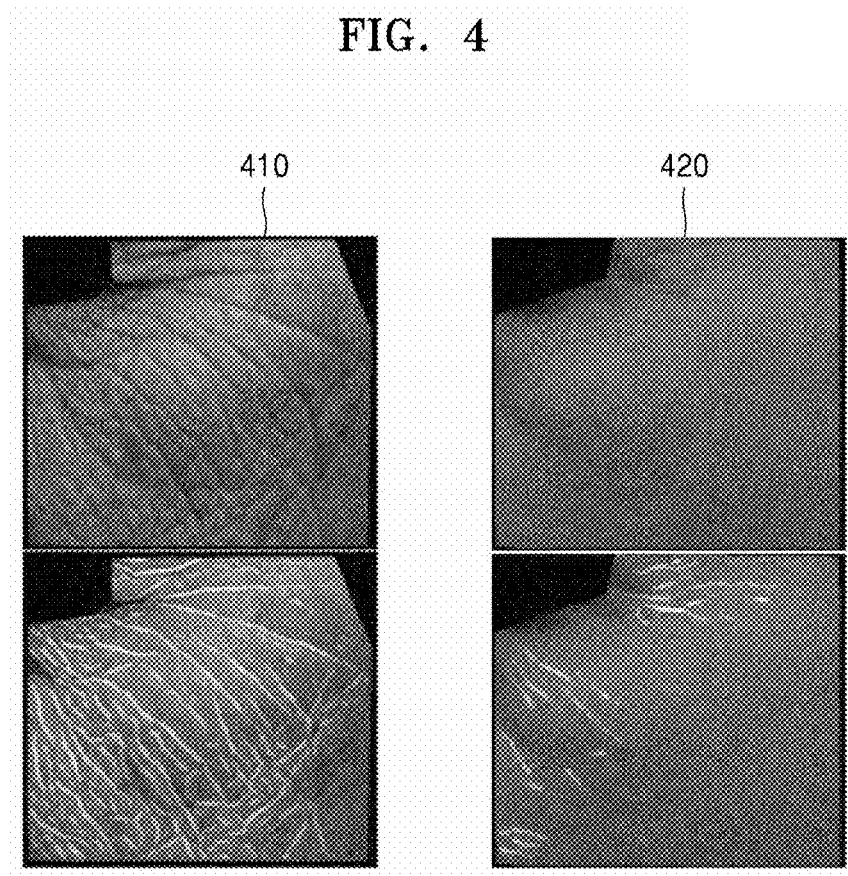
FIG. 4 illustrates visualization result differences according to sharpness of wrinkles, according to an embodiment.

FIG. 4 illustrates visualization result differences according to sharpness of wrinkles, according to an embodiment.

Referring to FIG. 4, an image 410 shows wrinkles identified by visualizing wrinkles in the skin including sharp wrinkles. An image 420 shows wrinkles identified by visualizing wrinkles in the skin including sharp wrinkles. According to an embodiment, not only sharp wrinkles, but also wrinkles that are unidentifiable with the naked eye.

Figure 5:
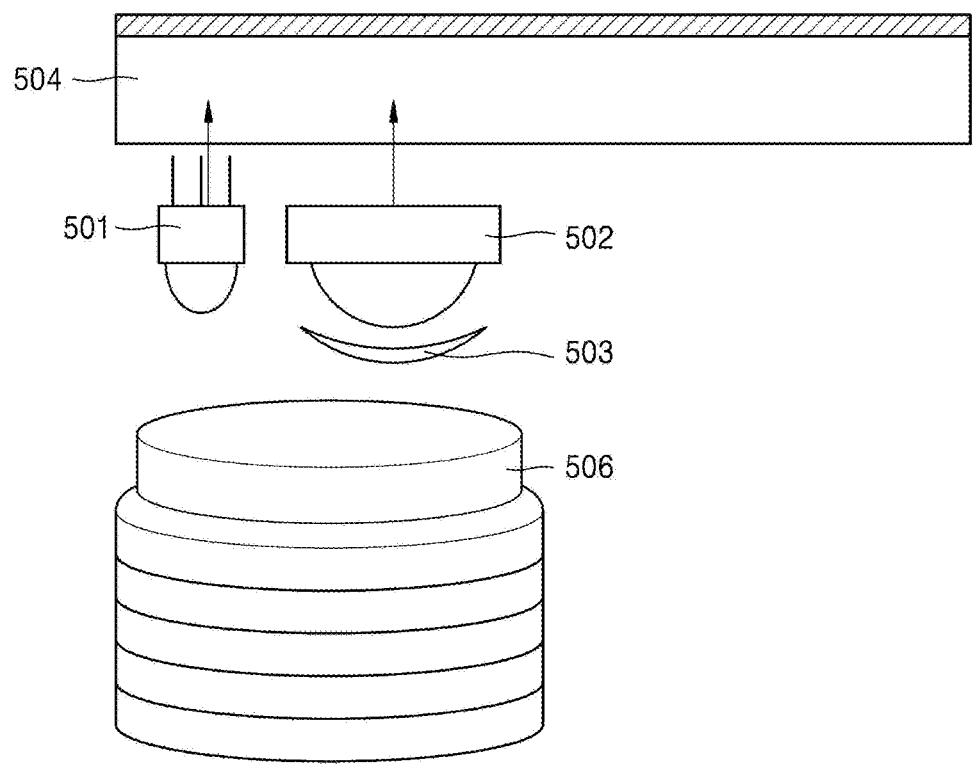
FIG. 5 illustrates an electronic device according to an embodiment.

FIG. 5 illustrates an electronic device according to an embodiment.

Referring to FIG. 5, a portable electronic device 500 may include a light source 501, a light detector 502, a lens 503, a processor 504, a display 505, and a shield portion 506.

The light source 501 emits light. In an embodiment, the light source 501 may irradiate light to the skin. The light may include white light.

The light detector 502 receives and detects light. In an embodiment, the light detector 502 detects the receiving light. In detail, the light detector 502 may detect light that is irradiated by the light source 501 and reflected and scattered by the skin.

The lens 503 may adjust the light received by the light detector 502. In an embodiment, the lens 503 may change focus of the light received by the light detector 502.

The processor 504 controls the operations of the light source 501, the light detector 502, and the display 505. Furthermore, the processor 504 may convert the light received by the light detector 502 to an electric signal and perform processing based on a specific algorithm.

In an embodiment, the processor 504 may normalize data about the reflection intensity of skin to a reference image of a reference standard white ($BaSO_4$) considering instability of the light source 501, for example, influence of battery charge, a spectrum change of a light source, a movement of a light source, or dust. Accordingly, instabilities, for example, tiny blemishes such as spots or other moles on the skin, a change in the amount of battery charge, a change in the intensity of spectrum of a light source, or dust may be disregarded through the above process.

The display 505 displays an image under the control of the processor 504.

The shield portion 506 shields, from other external light, an optical path through which the light irradiated by the light source 501 and reflected and/or scattered by the skin is returned to the light detector 502. In an embodiment, the shield portion 506 may include an opening for passing the light emitted by the light source 501 and the light received by the light detector 502. Furthermore, in an embodiment, the shield portion 506 may be opaque, have a certain shape, or have a hollow cylindrical shape having an opaque substrate having a bottom plate. Furthermore, the shield portion 506 may have a telescopic function, and the interior thereof may be applied or coated with a light absorbing material or a high reflective material or the shield portion 506 may be formed of a high reflective material. In an embodiment, an inner surface of the shield portion 506 may have diffuse reflectivity in a visible range of nor exceeding 4-5%. Furthermore, the inner surface that reflects light may have diffuse reflectivity in a visible range of not less than 95-99%.

Furthermore, the opacity of the shield portion 506 is one of major characteristics for determining measurement conditions. The opacity may be considered in the calculation of light transmission disregarding external illumination.

A surface coating type (absorption or reflection) is also a major parameter in the calculation of light transmission, but water of skin is dependent only on the skin type and the current function state. As unexpected multiple reflection contributes to a change of a final color of skin image, when absorption surface coating is used, all re-reflected illumination components may be excluded from the calculation. In contrast, in the case of a reflection surface, the contribution of unexpected multiple reflections may be taken into consideration and appropriate correction of a calculation algorithm may be performed. In any case, the reflection and absorption characteristics of a surface are opposite to each other (excluding or including light reflection) and are taken into consideration because any one of the reflection and absorption characteristics are used in the present disclosure.

In an embodiment, not all of the above-described constituent elements are necessary and some constituent elements may be omitted. For example, the light reflected and/or scattered by the skin may be directly received by the light detector 502 without the lens 503. Furthermore, for example, when the portable electronic device 500 is connected to other external device having a display, the display 505 may be omitted. However, this is merely an example and the present disclosure may vary in various ways.

Furthermore, in an embodiment, all or some of the above-described constituent elements may be provided as accessories of the portable electronic device 500. For example, the light source 501, the light detector 502, the lens 503, and the shield portion 506 may be provided as accessories that are attachable to the portable electronic device 500, not as parts of the portable electronic device 500. Alternatively, all of the light source 501, the light detector 502, the lens 503, the processor 504, the display 505, and the shield portion 506 may be provided as accessories that are attached to the portable electronic device 500. In this case, the accessories may be configured to be able to communicate with the portable electronic device 500.

Figure 6:
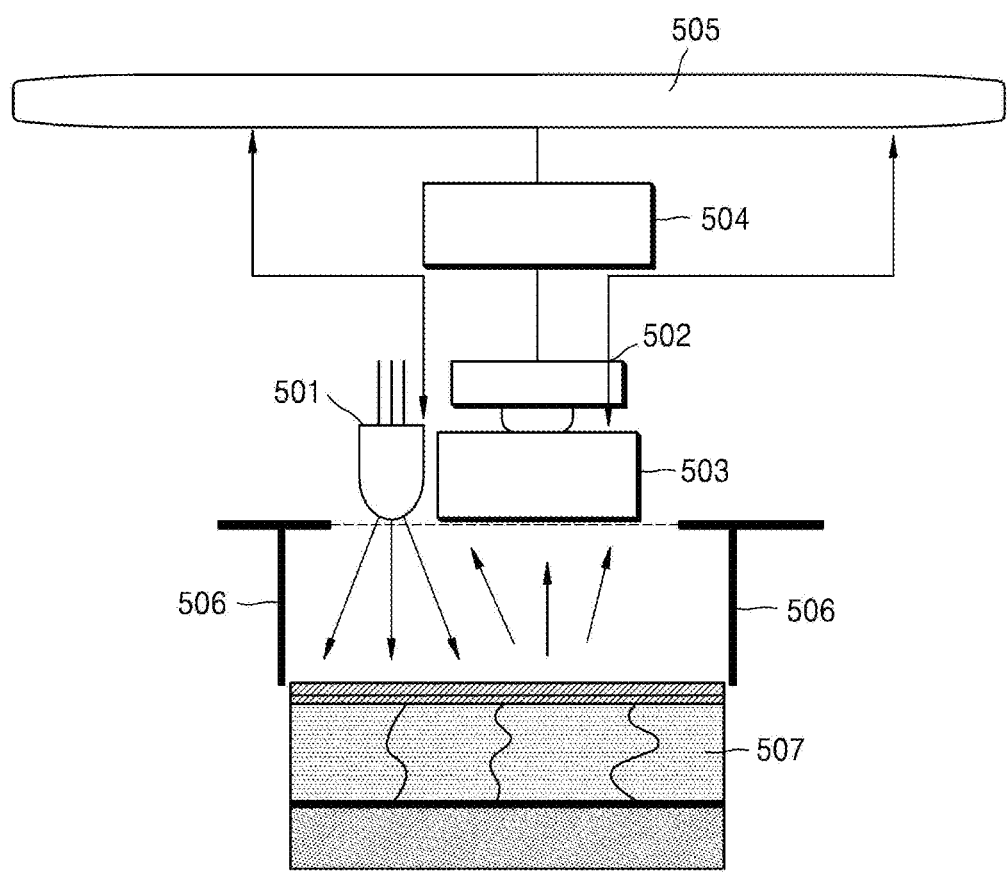
FIG. 6 illustrates a process of analyzing a skin state by using a portable electronic device according to an embodiment.

FIG. 6 illustrates a process of analyzing a skin state by using a portable electronic device according to an embodiment.

Referring to FIG. 6, the light source 501 irradiates light to skin 507, and the light irradiated to the skin 507 is reflected and/or scattered by the skin 507 and passes through the lens 503 to be received by the light detector 502. In this state, the shield portion 506 shields an optical path from other external light, thereby facilitating accurate analysis. The processor 504 may analyze a skin state by processing the light received by the light detector 502. In an embodiment, the processor 504 may set a color coordinate of a skin image and compare a result of the setting with a mathematical modeling result. In this case, the value of color may correspond to specific water of skin.

Figure 7:
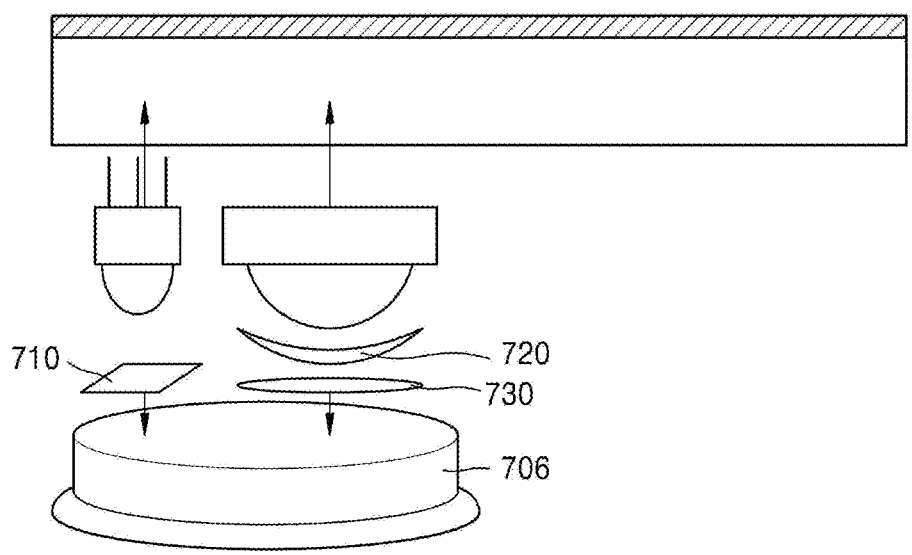
FIG. 7 illustrates a portable electronic device including optical elements, according to an embodiment.

FIG. 7 illustrates a portable electronic device including optical elements, according to an embodiment.

Referring to FIG. 7, the portable electronic device may include at least one of optical elements 710, 720, and 730. The optical element 710 may include a scattering plate or a lens. According to an embodiment, the size of a shield portion 706 may be reduced by using the optical elements 710, 720, and 730.

To reduce the size of the shield portion 706, in detail, the height of the shield portion 706, the size of a rear surface focus segment (a distance from a final surface to a rear surface focus) of an own optical system (OOS) used in an electronic device is reduced. To this end, a variety of the optical elements 710, 720, and 730 may be used. In detail, the own optical system of an electronic device is supplemented by a focus reducer, for example, an additional optical element. In terms of optics, the focus reducer is a convex lens and the reduction of a focal length may be calculated by the following equation.

$$R = 1 - D/FR,$$

Here, "R" denotes a reduction ratio of the focal length, "D" denotes a distance to an image plane, and "FR" denotes the focal length of an objective lens. For example, when an objective lens having a focal length of 100 mm is located 20 mm away from the image plane, the focal length may be reduced as follows.

$$R = 1 - 20/100 = 0.8$$

In an embodiment, the objective lens may be a colorless lens for detecting a macro image, or a general configuration of an objective lens (or a lens system) may be used therefor.

In FIG. 7, lenses 720 and 730 may be provided to reduce the focal length of a camera of the portable electronic device and may be smaller than the shield portion 706. The scattering plate may provide uniform illumination to the surface. At least some or all of the optical elements 710, 720, and 730 may be integrated in the shield portion 706. Furthermore, the shield portion 706 may have a lid having reference white therein.

As described above, the shield portion 706 may be provided separately from the portable electronic device or as an accessory of the portable electronic device. In this case, the shield portion 706 may be coupled to the portable electronic device by using a specific coupling method, which is described with reference to FIGS. 7 and 8.

Figure 8:
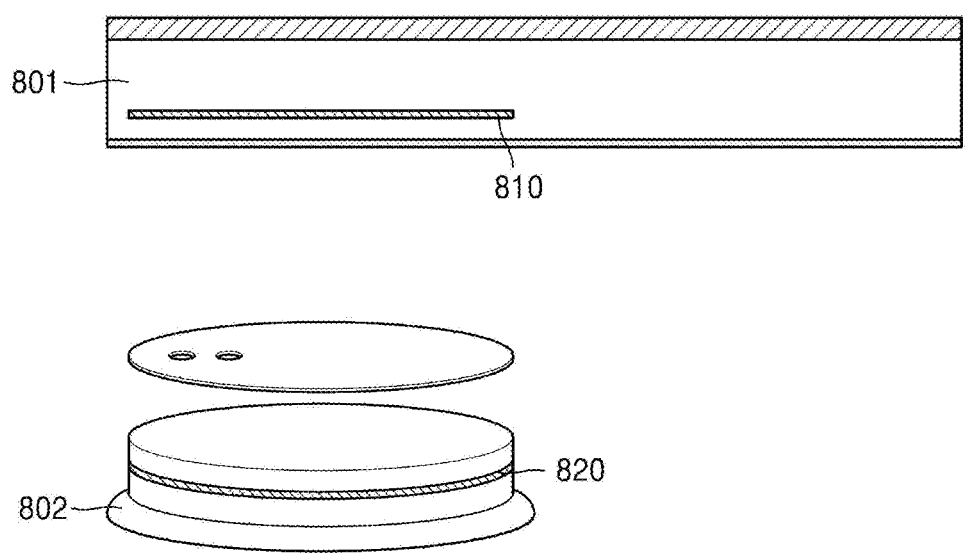
FIG. 8 illustrates that a portable electronic device and a shield portion are coupled to each other by using a magnetic link, according to an embodiment.
Figure 9:
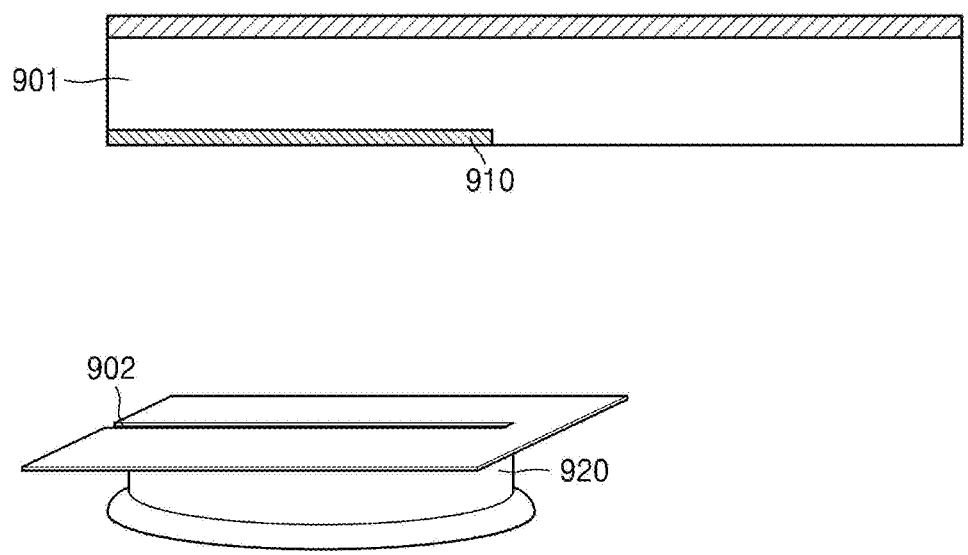
FIG. 9 illustrates that a portable electronic device and a shield portion are coupled to each other by using a slider, according to an embodiment.

FIG. 8 illustrates that a portable electronic device 801 and a shield portion 802 are coupled to each other by using a magnetic link, according to an embodiment. FIG. 9 illustrates that a portable electronic device 901 and a shield portion 902 are coupled to each other by using a slider, according to an embodiment.

As described above, all or some of the above-described constituent elements may be provided as accessories of the portable electronic device. In FIGS. 8 and 9, the shield portions are provided as accessories attachable to the portable electronic device. In this case, the shield portion and the portable electronic device may be coupled to each other in various methods.

First, referring to FIG. 8, the portable electronic device 801 and the shield portion 802 may be coupled to each other by using a magnetic link, that is, a magnet. In an embodiment, the portable electronic device 801 may include a metal plate 810, and the shield portion 802 may include a magnetic plate 820. The portable electronic device 801 and the shield portion 802 may be coupled to each other by the metal plate 810 and the magnetic plate 820. In contrast, the portable electronic device 801 may include a magnetic plate, and the shield portion 802 may include a metal plate. In detail, the portable electronic device 801 may include the metal plate 810 under a rear surface of a main body. Furthermore, the shield portion 802 may include the magnetic plate on a surface thereof.

Referring to FIG. 9, the portable electronic device 901 and the shield portion 902 may be coupled to each other by using a slider. In an embodiment, the portable electronic device 901 may include a guide 910, and the shield portion 902 may include a guide groove 920. The portable electronic device 901 and the shield portion 902 may be slidably coupled to each other. In contrast, the portable electronic device 901 may include a guide groove, and the shield portion 902 may include a guide.

Figure 10:
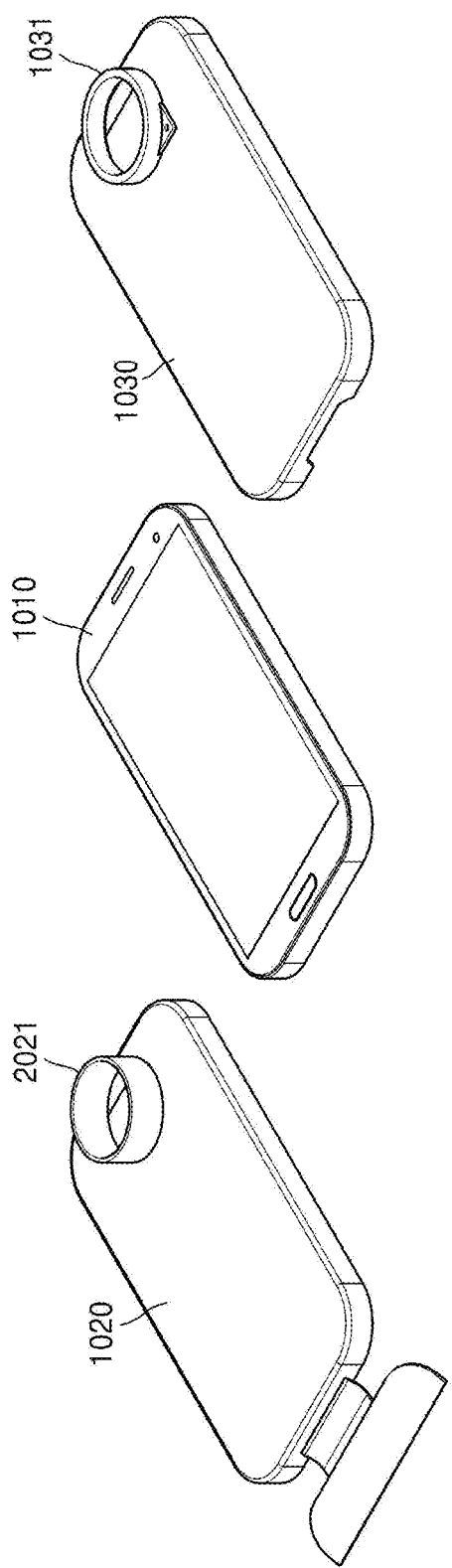
FIG. 10 illustrates a shield portion configured as an accessory attachable to a portable electronic device, according to an embodiment.

FIG. 10 illustrates a shield portion configured as an accessory attachable to a portable electronic device, according to an embodiment.

Referring to FIG. 10, a mobile phone 1010 is illustrated as the portable electronic device, and accessories 1020 and 1030 attachable to the portable electronic device are illustrated. Shield portions 1021 and 1031 for analyzing a skin state are respectively formed on the accessories 1020 and 1030. Although FIG. 10 illustrates the mobile phone 1010 as the portable electronic device, the portable electronic device is not limited thereto and may include notebook computers, tablets, mobile terminals, or smartphones. Furthermore, although FIG. 10 illustrates the accessories 1020 and 1030 as portable phone cases, the portable phone case is not limited thereto and accessories having a variety of shapes may be used. For example, only the shield portions 1021 and 1031 may be provided as separate accessories.

Figure 11:
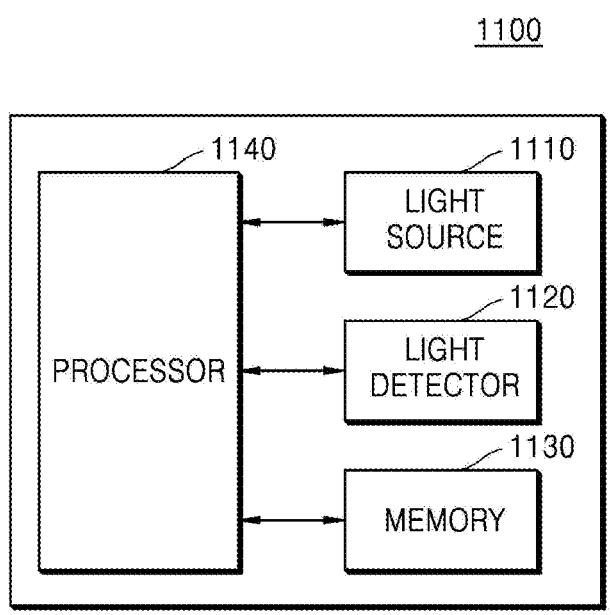
FIG. 11 is a block diagram of a configuration of a portable electronic device according to an embodiment.

FIG. 11 is a block diagram of a configuration of a portable electronic device 1100 according to an embodiment.

Referring to FIG. 11, the portable electronic device 1100 according to an embodiment may include a light source 1110, a light detector 1120, a memory 1130, and a processor 1140.

The light source 1110 emits light. In an embodiment, the light source 1110 may irradiate light to the skin. Furthermore, the light source 1110 may emit light having a different wavelength as needed. Furthermore, the light source 1110 may include one or more light sources. When a plurality of light sources exist, the respective light sources may emit light of the same wavelength or different wavelengths.

The light detector 1120 may receive and detect light. In an embodiment, the light detector 1120 detects the received light. In detail, the light detector 1120 may detect the light that is irradiated by the light source 1110 and reflected and/or scattered by the skin. Furthermore, the light detector 1120 may detect light emitted from the skin.

The memory 1130 may store a program and data needed for the operation of the portable electronic device 1100. Furthermore, the memory 1130 may store the data processed by the portable electronic device 1100. The memory 1130 may include a storage medium such as ROM, RAM, hard disk, CD-ROM, and DVD or a combination of the storage media. Furthermore, the memory 1130 may include a plurality of memories. In an embodiment, the memory 1130 may store instructions executable in the processor 1140.

The processor 1140 may control a series of processes of the portable electronic device 1100. In an embodiment, the processor 1140 may execute a program stored in the memory 1130 to irradiate light to the skin, to detect light received from the skin, and to analyze a skin state based on the detected light. Furthermore, the processor 1140 may generate an image by processing the light detected by the light detector 1120.

The processor 1140 may determine quantitative (brightness) and qualitative (color) color characteristics of skin by using colorimetric systems. The processor 1140 may determine three colors coordinates R, G, and B in units of pixels by using the colorimetric systems to measure reflectivity of skin with respect to each skin image. Then, the processor 1140 may convert the three color coordinates to color coordinates X, Y, and Z of colorimetric systems MKO1931 (Yxy) and color coordinates L*, a*, and b* of colorimetric systems MKO1976 (L* a* b*) by using a simple ratio. In the human skin, contents of melanin, hemoglobin, and water may be evaluated by using an algorithm based on the solution of reverse Monte-Carlo problem. When the algorithm is used, at least two layer models of skin may be considered with respect to all parts of the body. The processor 1140 may calculate a reflection coefficient of skin by using the Monte-Carlo method in a visible spectrum range. Then, the spectrum is recalculated in the color coordinates system and compared with experiment data regarding the reflectivity of skin, and thus matching between the color coordinates and each spectrum may be determined. The contents of melanin, hemoglobin, and water of skin may be evaluated through the above process. Furthermore, the RGB values are converted to trichromatic values in the color space that is a device-independent color system compatible with the RGB work space (NTSC, sRGB, etc.). To set the relationship between the concentrations of melanin, water, and blood and the trichromatic values XYZ, Monte-Carlo modeling (MCM) of radiation transport with respect to the human skin model may be used.

The structure of a spectrum of light penetrating biological tissue depends on detection geometry, specific experiment conditions including a plurality of parameters of incident light radiation, and the concentration and spatial distribution of a chromophore in tissue. In an embodiment, the processor 1140 may use a specially designed calculation method to model a visible reflection spectrum of skin and calculate skin color. In this state, the calculated data is compared with the experiment data obtained in the measurement of an extended dynamic range through various portions of a human body.

Considering the actual conditions for detection and very complex structure of tissue in the present disclosure, there is no general analysis solution capable of simulating interactions between the detected scattered light, tissues with the scattered light, structural disorder, and/or a physiological change. Accordingly, a stochastic Monte-Carlo modeling (MCM) may be used. In the present disclosure, an object-oriented Monte-Carlo modeling is used which can describe photons and structural components of tissue as mutually interacting objects. Accordingly, an object (photon) is propagated through an object (medium or interlayer) and interacts with a constituent element, such as, a cell, a blood vessel, or a collagen fiber of the object (medium or interlayer). The expression of a medium by the object enables development of a practical model of tissue that indicates a three-dimensional spatial change of a biological structure. A multilayered model of tissue is applied for modeling a transmission spectrum. The model that is known as a conventional technology extends to 17 layers by including muscle and bone structures.

The Monte-Carlo modeling may be performed considering an actual geometrical shape of a probe used for an experiment by using at least $10^{10}$ packets of photons. A conversion of spectrum power distribution to CIE XYZ (CIE 1976 L*a*b*) coordinates and RGB color values can be performed using the standard CIE 2° system and the trichromatic values of the light source used. Observation of the effects of tissue color changes caused by changes in water and oxygen of blood may potentially be used in practical diagnosis and bioengineering applications.

Such a change may be quantified and characterized by the developed Monte-Carlo modeling. The major points of the modeling are as follows.

1) Visualization of skin under certain conditions of photodetection is ensured by the use of a specially designed hood for the object.

2) Numerical experiments on light transmission in the skin are performed on known light detection conditions and light sources, and results thereof are the number of spectra and the respective color coordinates with respect to the different amounts of skin chromophore.

3) The captured color coordinates are compared with the color coordinates and each spectrum obtained through numerical modeling.

The (numerically obtained) comparison data already contains information on the concentrations of melanin, water, and blood for a specific image of skin. Accordingly, when match is detected while comparing the coordinates, the concentration of chromophore may be determined.

Relationship Between RGB Value and Chromophore Concentration of Skin

The RGB value of a pixel on a skin surface image generated by a digital camera can be expressed as follows.

$$\begin{pmatrix} R \\ G \\ B \end{pmatrix}^T = L_1 \times \begin{pmatrix} X \\ Y \\ Z \end{pmatrix}^T \text{ where,}$$

$$X = \int_{400}^{700} E(\lambda)\bar{x}(\lambda)0(\lambda)d(\lambda),$$

$$Y = \int_{400}^{700} E(\lambda)\bar{y}(\lambda)0(\lambda)d(\lambda), \text{ and}$$

$$Z = \int_{400}^{700} E(\lambda)\bar{z}(\lambda)0(\lambda)d(\lambda)$$

are trichromatic values in CIE XYZ color system, and $(\ldots)^t$ is a vector transposition. $L_1$ is a transformation matrix to transform the XYZ values to RGB values corresponding thereto and exists for each work space (NTSC, PAL/SECAM, or sRGB). $\lambda$, $e(\lambda)$, and $0(\lambda)$ denote the wavelength of a light source, a spectrum distribution (for example, absolute luminosity spectrum of a diode), and a diffusion reflection spectrum of skin, respectively. $x(\lambda)$, $y(\lambda)$, and $z(\lambda)$ are functions of color match in the color system CIE XYZ. Integration takes place at a wavelength (400-1000 nm) of visible and near-infrared ranges. Assuming that the skin tissue consists mainly of epidermis containing melanin and dermis containing blood or water, which are not to be considered, the diffusion reflection of skin tissue may be expressed as follows.

$$0 = \frac{I}{I_0} = \left[ \int_0^\infty P_e(\mu_{s,e}, g_e, l_e)\exp(-\mu_{a,m}l_e)dl_e \right] \times \left[ \int_0^\infty P_d(\mu_{s,d}, g_d, l_d)\exp(-\mu_{a,b}l_e)dl_d \right]$$

Here, $I_0$ and $I$ are intensities of the standard reflected light and detected light, respectively. $P(\mu_s, \mu_g, i)$ is a probability function of the path length depending on the scattering characteristics and the geometry of the measurement. $\mu_s$, $\mu_g$, g, and l respectively denote a scattering coefficient, an absorption coefficient, an anisotropic coefficient, and a path length of photons. Indexes w, m, b, e, and d respectively denote water, melanin, blood, epidermis, and dermis. The absorption coefficient of each chromophore is expressed by a multiplication of a concentration C, a light absorption coefficient $\varepsilon$, and $\mu_a = c\varepsilon$. Accordingly, the RGB values are expressed by functions of $C_w$, $C_m$, and $C_b$.

The following procedure is used when the concentration of chromophore is evaluated in the skin based on the RGB image. First, the RGB values of each pixel in the skin image are converted to the XYZ values using a matrix $N_1$ as follows. In each pixel of an image, $$\begin{pmatrix} R \\ G \\ B \end{pmatrix} = N_1 \times \begin{pmatrix} X \\ Y \\ Z \end{pmatrix}.$$

Then, the matrix $N_1$ has 24 color components and is determined based on the measurement of a color checker standard that provides data for providing the CIE XYZ value for each component under specific illumination and in a corresponding reflection spectrum. Furthermore, the X, Y and Z values are converted to $C_w$, $C_m$, and $C_b$ by using the matrix $N_2$.

Next, in the diffusion values of $C_w$, $C_m$, and $C_b$, the diffusion reflection spectrum $o(\lambda)$ is calculated in a wavelength range of 400 to 1000 nm at an interval of 5 nm by the Monte-Carlo modeling for light transmission in skin tissue, and corresponding X, Y, and X values are obtained. In this Monte-Carlo modeling, a melanin absorption coefficient for $C_m$ is introduced into the epidermis as $\mu_a$ and m, a blood absorption coefficient for $C_b$ is introduced as $\mu_a$ and B in the dermis, and a water absorption coefficient for $C_w$ is introduced as $\mu_a$ and w in the dermis. The thicknesses of epidermis and dermis layers are defined to be 0.05 and 5.05 mm, respectively, and the refractive index of each layer is set to 1.4. Then, the XYZ values are calculated based on the modeled $o(\lambda)$. The calculation is performed on various combinations of $C_w$, $C_m$, and $C_b$ to obtain a data set of concentration and XYZ values of the chromophore. Multiple regression analysis using data sets shows two regression equations for $C_m$ and $C_b$.

$$Cm = a0 + a1x + ay + a3z,$$

$$Cb = bo + b1x + b2y + b3z.$$

$$Cw = wo + w1x + w2y + w3z.$$

Regression coefficients ai and bi (i=0, 1, 2, 3) each reflect contribution of the XYZ values in $C_w$, $C_m$, and $C_b$ and are used as components of 4×3 matrix $N_2$. Accordingly, with the help of $N_2$, the conversion from the trichromatic values to the chromophore concentration is expressed as follows.

$$\begin{pmatrix} C_m \\ C_b \\ C_w \end{pmatrix} = N_2 \times \begin{pmatrix} X \\ Y \\ Z \\ 1 \end{pmatrix}$$

After the matrixes $N_1$ and $N_2$ are determined, the image $C_w$, $C_m$, and $C_b$ may be reconstructed without the Monte-Carlo modeling.

In an embodiment, considering the instability of the light source 1110 (the impact of battery charge, a change of spectrum of a light source, a movement of a light source, or dust), the processor 1140 may normalize data about the reflection intensity of skin to a reference image of a reference standard white ($BaSO_4$). Tiny blemishes such as spots or other moles and instability such as a change in the battery charge amount, a change of the intensity of a light source, or dust may be ignored by the above process.

Furthermore, although not illustrated in FIG. 11, the portable electronic device 1100 may further include an additional constituent element. For example, the portable electronic device 1100 may further include a display, a shield portion, at least one filter, a communication unit, and so forth.

In an embodiment, the display may display an analysis result under the control of the processor 1140. The display may display information about the content of chromophore for a target skin. The information may include a warning about the need to provide water to the sunburn or skin, as well as various pieces of advice on how the user's skin can be protected. The information may be displayed in a variety of ways. For example, a concentration may be expressed in a numerical form or in a two-dimensional color distribution diagram. Furthermore, the information about a skin state may be transmitted to the outside via communication unit. Information related to advice and treatment about the skin state may be received through the information that is transmitted to the outside.

In an embodiment, the shield portion may shield the light irradiated by the light source 1110 to skin and the light from the skin that is received by the light detector 1120 from the outside. In an embodiment, the shield portion may include an opening to pass the light emitted from the light source 1110 and the light received by the light detector 1120. Furthermore, in an embodiment, the shield portion may be opaque, have a certain shape, or have a hollow cylindrical shape having an opaque substrate having a bottom plate. Furthermore, the shield portion may have a telescopic function, and the interior thereof may be applied or coated with a light absorbing material or formed of a high reflective material. According to an embodiment, the skin state, for example, chromophore concentration, may be analyzed by using the shield portion under any external condition (natural light, artificial illumination, no illumination).

In an embodiment, the filter may include a first filter and a second filter. The first filter may filter the light irradiated by the light source 1110 to skin, and the second filter may filter the light from the skin that is received by the light detector 1120. Accordingly, the first filter may be located between the light source 1110 and the skin, and the second filter may be located between the skin and the light detector 1120.

In an embodiment, the first filter may include a first polarization filter and a second polarization filter. The first polarization filter and the second polarization filter may be a polarization filter for selecting a fixed polarized component and a polarization filter for selecting a polarized component of the light from the skin that is received by the light detector. In this case, the polarization filter which enables selection of a polarized component of light may be operated under the control of the processor 1140. When the portable electronic device 1100 includes the first polarization filter and the second polarization filter, the light detector 1120 may detect the light of a polarized component, and the processor 1140 may analyze the expression form of skin based on the detected polarized component.

In an embodiment, the processor 1140 may determine a depolarization ratio of the light irradiated to skin through the first polarization filter and the light received by the light detector through the second polarization filter, and detect wrinkles of skin based on the depolarization ratio. In this case, the processor 1140 may control the first polarization filter and/or the second polarization filter such that the polarized components of the first polarization filter and the second polarization filter are in the same direction and in a vertical direction, and determine the depolarization ratio by comparing the polarized component detected by the light detector 1120 in the same direction as and the polarized component in a direction perpendicular to the direction in which the polarized light irradiated to the skin.

In an embodiment, the first filter may include a filter for transmitting light of a wavelength range for exciting porphyrin, and the second filter may include a filter for transmitting light of a wavelength range for emitting the excited porphyrin. In this case, the light detector 1120 may detect the light transmitted through the second filter, and the processor 1140 may analyze the purity of skin (purity) based on the detected light.

In an embodiment, the light source 1110 may include a light source that irradiate light in a wavelength range for exciting porphyrin, and the second filter may include a filter for transmitting light in a wavelength range for emitting the excited porphyrin. In this case, the light detector 1120 may detect the light transmitted through the second filter, and the processor 1140 may analyze the purity of skin based on the detected light. In this state, the processor 1140 may analyze a distribution of porphyrin in the skin based on the intensity of the detected light and determine the purity of skin based on the distribution of porphyrin in the skin.

In an embodiment, the light source 1110 may include a light source for irradiating near-infrared light, and the light detector 1120 may include at least one near-infrared detector for detecting near-infrared light received from the skin. In this case, the processor 1140 may analyze a water state of the skin based on the near-infrared light detected by the near-infrared detector. In this state, the processor 1140 may determine the reflectivity of skin based on the detected near-infrared light and analyze the water state of the skin based on the reflectivity of skin.

Figure 12:
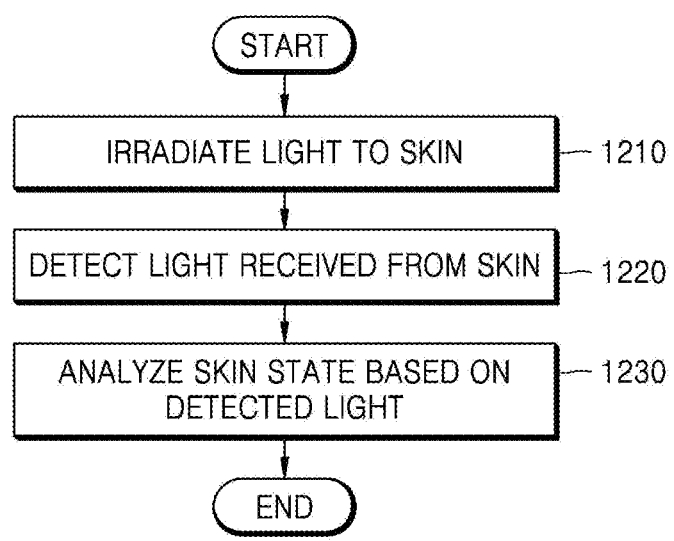
FIG. 12 is a flowchart for describing a method of operating a portable electronic device, according to an embodiment.

FIG. 12 is a flowchart for describing a method of operating a portable electronic device, according to an embodiment.

Referring to FIG. 12, in operation 1210, the portable electronic device irradiates light to the skin, and in operation 1220, the light received from the skin is detected. In an embodiment, the light source may include a linear polarization filter and irradiate light of a polarized component to the skin. Furthermore, the light detector may include a complementary metal-oxide-semiconductor (CMOS) camera, and may further include a liquid crystal polarizer for electrically rotating a polarization angle by a polarization angle of 90° in a direction parallel to a polarization surface of the polarization filter of the light source (that is, a crossed orientation of the polarization planes may be generated).

In operation 1230, the portable electronic device may analyze a skin state based on the detected light. The portable electronic device may process a captured image by analyzing the intensity in the image that is executed.

In an embodiment, the operation 1210 may include irradiating polarized light to the skin, and the operation 1220 may include selectively receiving polarized components that are in the same direction as and in the direction perpendicular to the direction in which the polarized light is irradiated to the skin. In this state, the operation 1230 may include determining a depolarization ratio by comparing a polarized component in the same direction as and a polarized component in the direction perpendicular to the direction in which the polarized light irradiated to the skin, and detecting wrinkle of skin based on the depolarization ratio.

In an embodiment, the portable electronic device may very fast and continuously capture face images for two polarization states. As a result, in the images obtained by the portable electronic device, the position and angle of a face in directions parallel to and crossing a polarization surface are the same and corresponding pixels in two images may be compared with each other by using image processing to search for a surface reflection component.

In an embodiment, to determine an anisotropic parameter in a skin area having a correlation with a photo age of the human skin, the operation method may further include determining a depolarization ratio of light reflected from the human skin surface and dispersed therein by using data about a degree of rotation of polarization surface of the scattered light after a skin area is detected. Furthermore, the operation method may further include determining the depth of wrinkles in the skin area, the length of wrinkles, the density of wrinkles, and the characteristic coefficient of the distribution of wrinkle clusters using the analysis of the image of the pixel intensity and the spatial distribution of the values thereof.

Furthermore, although not illustrated in FIG. 12, the method of operating a portable electronic device may further include displaying the resultant data of the characteristic coefficient of the human skin area on the screen, visualizing wrinkles, optionally displaying an image of the entire human skin area of interest or an image of the entire human face, displaying text information about characteristics of the wrinkles on the skin area, and displaying information about dermatological advice and recommended beauty treatments. Furthermore, in an embodiment, in the method of operating a portable electronic device, the photo age of the human skin area may be monitored based on data and the result of the displaying of the characteristic coefficient of skin area.

The above method may be performed in detail as follows.

1) Polarization Photographing of Skin

As described above, the wrinkle signifies a sudden depth change of a local skin surface at a specific position. Accordingly, a skin image is recorded such that the detected signal, that is, reflected and/or scattered by the skin a strength vector of a detected signal, that s, the light detected by being reflected and/or scattered by the skin is aligned in the same direction as the strength vector of a probing beam that is the light irradiated to the skin. Accordingly, the polarization surface of an analyzer (for example, Polaroid) that is located in front of a detection apparatus (for example, a light detector) is in the same direction as (that is, parallel to) the polarization surface of a polarizer located in the rear of a probing source (for example, a light source). Alternatively, when the source generates linear polarized radiation, a common component of the backward scattered light is transferred.

The process is needed to divide the detected signal into two parts, and the detected signal may be divided into a Fresnel component and a diffuse component. The Fresnel component denotes a component having no change in the polarization state (that is, a portion reflected by the skin, including all blemishes (wrinkles)), and the diffuse component denotes an at least partially depolarized component (formed by scattering of light in a layer around the skin surface). By filtering the diffuse component of the detected light, the light reflected by the skin surface is "amplified".

2) Determining Incoming Digital Data

As the electronic device includes a camera (CMOS or CCD), a flash (one or more LEDs), and an ADC, a process of receiving and processing a digital signal is needed. The electronic device may receive three signals corresponding to three basic color channels (red, blue, and green, RGB) (because the light detector includes a Baeyer filter). The electronic device may select a red channel (blue and green channels are ignored) including information about the shape of a skin surface with minimum information about constituent elements (melanin or blood) for processing and analyzing signals.

3) Increasing Contrast of an Image

The electronic device may adjust contrast of an image by using automatic control of a histogram inclination (spatial distribution of brightness) of pixel intensity. This does not affect the overall contrast of the image and may increase an analyzed dynamic range of the brightness of a pixel.

4) Normalization of an Image

The electronic device may normalize a resultant image of skin to have a previously selected average value and a variance value. The process is needed to standardize the distribution of a dynamic gray scale level and facilitate additional processing, without modifying the image structure.

5) Assessment of Local Orientation of Wrinkles

The electronic device may identify, that is, obtain information about the local direction of characteristics in form of an image. A mathematical least squares method may be applied to the process. The evaluation of a local direction of wrinkles may include sub-steps as follows.

5.1. Forming (selecting) a window from a value of an adjacent pixel to each pixel of an image.

5.2. Calculating a gradient value to two available directions (x and y) to each pixel in the window.

5.3. Evaluating the local direction of a center pixel by a least squares method.

5.4. Converting the image obtained in the previous step to a continuous vector filed by calculating sine and cosine of the value of a local direction at a specific position of the image.

In this state, the obtained value may be expressed as follows.

co (i, j)=cos (o (i, j)) and so (i, j)=sin (o (i, j)). o (i, j) is a calculated direction with respect to coordinates (i, j).

5.5. Smoothing a vector field to convolution having a derivative of a Gauss function.

The obtained values may be expressed by gso (i, j) and gso (i, j).

5.6. When the resultant direction is calculated with an arctangent of a ratio, gco (i, j)/gso (i, j) is produced and expressed by o (i, j).

Aside from information about the local direction with respect to non-homogeneities of an image, the evaluation of the local direction of wrinkles may include evaluating reliability, that is, checking information about how accurately the local direction is evaluated. The reliability in the evaluation of the direction is determined by covariance momentum of a relatively center (that is, selected) pixel with respect to a neighboring pixel.

6) Determination of Frequency of Wrinkles

The electronic device may evaluate the frequency of wrinkles in an image. The image is divided into small blocks of pixels, and an intensity value for each block is projected in a direction perpendicular to an average direction of the blocks. When an image includes elongated peculiarities (that is, the characteristics, specifically, wrinkles), the projection may indicate a sinusoidal function having a local minimum value corresponding to the wrinkles in the image. The frequency of the determined function corresponds to the frequency of local non-homogeneities to each image block.

7) Improvement of Image Quality by Gabor Filtering

The electronic device may apply a Gabor filter with a direction and a frequency similar to those determined to a current pixel, with respect to each pixel of an image in which an estimated frequency have a true value (that is, a positive value). The shape of wrinkle characteristics in an image may be improved through the above process. The Gabor filtering may be used to detect a boundary of an object to improve the quality of an image.

8) Detection of Wrinkles

The electronic device may binarize an obtained resultant image to a threshold value defined by a percentage of the maximum value in an analyzed source image The obtained binarized image may be a wrinkle mask as a wrinkle exists in an image area where a pixel value is 1 and no wrinkle exists where a pixel value is 0.

9) Quantitative Evaluation of Wrinkles

The electronic device may define the number of wrinkles in the binarized image scaled in the total area to be a total number of pixels having a value of 1. Furthermore, a pixel having a value of 1 adjacent to a previous pixel may be counted to evaluate continuity of the wrinkle. Such a wrinkle evaluation method determines only the number and degree of branches, without considering the depth of a wrinkle. A resultant map of a wrinkle may be divided into three classes and nine subclasses according to the Fitzpatrick scale of a wrinkle.

In an embodiment, in the operation 1210, light in a wavelength range for exciting porphyrin is irradiated to the skin, and in the operation 1220, light in a wavelength range for emitting the excited porphyrin is detected. In this state, in the operation 1230, distribution of porphyrin in the skin is analyzed based on the intensity of the detected light and the purity of skin is determined based on the distribution of porphyrin in the skin.

In an embodiment, in the 1210, near-infrared (NIR) light is irradiated to the skin, and in the operation 1220, the NIR light received from the skin is detected. In this state, in the operation 1230, reflectivity of skin is determined based on the detected NIR light and a water state of the skin is analyzed based on the reflectivity of skin.

In an embodiment, the NIR light may be irradiated to the skin through a NIR LED mounted on the portable electronic device. The NIR LED interacts with the human skin area through absorption, reflection, and scattering and emits light received by a NIR detector. The quantitative, qualitative characteristics of skin water are determined by the analysis of a signal reflected from the skin at different wavelengths of a NIR range.

In an embodiment, the portable electronic device images the light received by the NIR detector and forms two or more arrays used for a future process from the obtained image, that is, at least two images corresponding to the boundary of a selected spectrum range. As the image indicates at least a part of skin area, the size of array may be changed. Accordingly, the portable electronic device may perform alignment to cut off an area having a specific coordinate.

In an embodiment, the portable electronic device removes noise from an image by using a filter, for example, a Gabor filter, a central value), and automatically identifies an area corresponding to "white" in the obtained resultant image. An area in which a white light brightness level, that is, a reflection coefficient, is 100% may be determined by averaging brightness values in these areas. After all array components are normalized to a white brightness value, the array formed in each component is a reflection coefficient of an object. Those having a reflection coefficient value exceeding 100% are excluded (may be delayed by irregular illumination).

In an embodiment, the portable electronic device may determine an optical density of a spectrum range selected from a skin area (Optical density is the logarithm of the magnitude of the inverse of the reflection coefficient of a selected wavelength) by using an array of the reflection coefficient obtained to determined a water concentration in the skin area. The spectrum range may be selected such that the start thereof corresponds to the minimum absorption of a major chromophore and the end thereof corresponds to the maximum absorption of water. Then, by determining inclination of a time signal of the optical density, water concentration dynamics in the skin area may be determined.

In an embodiment, the portable electronic device may determine the characteristic coefficient of water in the skin area (that is, a different image) and display resultant data of the characteristic coefficient of skin area. Furthermore, the portable electronic device may display a skin area of a selective interest or the entire face image, visualize a water distribution in the face skin, display text information about water of skin, and display information about dermatological advice and recommended beauty treatments. As a result, the portable electronic device may monitor water in the human skin area based on the resultant data of the characteristic coefficient of the displayed human skin.

The above method may be performed in detail as follows.

Skin reflection in the infrared area of a spectrum may be distinguished based on the evaluation of a reflection coefficient at a specific wavelength normalized to a skin reflection coefficient of the forehead. In this case, the most distinguished point may be obtained by measuring reflection at a wavelength of about 1310 nm and about 1470 nm corresponding to a spectrum range having the minimum and maximum water absorptions. The measurement of a reflection coefficient of skin used for calculating the water concentration of skin is not much effective because individual characteristics of a user skin, furthermore, metabolism characteristics of a human, are not considered.

In an embodiment, the portable electronic device may evaluate the ratio of reflection coefficients of different skin areas such as eyelids/forehead or eyelids/cheeks to determine the water concentration. In this case, the water concentration ratio for each skin area may be constant. For example, the normalized reflection coefficient of skin at the eyeball is always smaller than 1, but always greater for the cheeks.

In an embodiment, the portable electronic device may measure a diffusion reflection spectrum of a wavelength range of about 950-1500 nm in the skin of the forehead, cheeks, chin, elbow, forearm, palms, knees, and heels by using a spectrophotometric method of a Fourier transform of the NIR range. Then, the portable electronic device may compare local differences in the skin water calculated from the peak height of water at a wavelength range of about 980 nm normalized to the peak height of the wavelength range of about 1450 nm.

As a result, the portable electronic device may obtain a relative skin water ratio such that 0 corresponds to a dry skin and a maximum value is a value corresponding to skin saturated with water.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope as defined by the following claims.

The invention claimed is:

1. A portable electronic device comprising:
   a display;
   a light source configured to radiate light to skin;
   at least one light detector configured to detect light received from the skin;
   at least one memory storing instructions;
   a first polarization filter configured to filter the light radiated to the skin from the light source;
   a second polarization filter configured to filter the light received from the skin by the at least one light detector; and
   a processor configured to execute the instructions to:
   control the light source to radiate the light,
   analyzing the skin for wrinkles on a surface of the skin based on a depolarization ratio of the light detected by the at least one light detector, and
   control the display to display a highlighting of the wrinkles based on analyzing the skin for the wrinkles,
   wherein the light received from the skin comprises at least one of light scattered, light reflected, and light emitted by the skin,
   wherein the second polarization filter is configured to, under the control of the processor, select a polarized component of the light received from the skin,
   wherein the at least one light detector is further configured to detect light of the selected polarized component,
   wherein the processor is further configured to execute the instructions to:
      control the second polarization filter to select a polarized component in each of a same direction as and a direction perpendicular to the first polarization filter,
      determine the depolarization ratio by comparing the polarized component in the same direction as the polarized light radiated to the skin and filtered by the first polarization filter with the polarized component detected by the at least one light detector in the direction perpendicular to the polarized light radiated to the skin and filtered by the first polarization filter, and
      detect the wrinkles on the surface of the skin based on the depolarization ratio.

2. The portable electronic device of claim 1, further comprising:
   a shield portion configured to shield, from the outside, the light radiated to the skin and the light received from the skin; and
   wherein the processor is further configured to execute the instructions to control the display to display an analysis result.

3. A portable electronic device according to claim 1, wherein the processor is further configured to execute the instructions to control the display to display the highlighting of the wrinkles by at least one of overlaying the highlighting of the wrinkles onto an image of the skin and displaying the highlighting of the wrinkles without displaying the image of the skin.

4. A method of operating a portable electronic device, the method comprising:
   radiating light to skin;
   detecting light received from the skin;
   analyzing the skin for wrinkles on a surface of the skin based on determining a depolarization ratio of the detected light; and
   displaying a highlighting of the wrinkles based on analyzing the skin for the wrinkles,
   wherein the radiating of light to the skin comprises radiating polarized light to the skin,
   wherein the detecting the light received from the skin comprises selecting and receiving a polarized component in each of a same direction as and a direction perpendicular to the polarized light radiated to the skin, and
   wherein the analyzing of the skin comprises:
   determining the depolarization ratio by comparing the polarized component in the same direction as the polarized light radiated to the skin with the polarized component in the direction perpendicular to the polarized light radiated to the skin; and
   detecting the wrinkles on the surface of the skin based on the depolarization ratio.

5. A computer program product comprising a non-transitory recording medium having a program stored therein for performing the operation of the portable electronic device of claim 4.

* * * * *